United States Patent
Wang et al.

(10) Patent No.: US 9,119,717 B2
(45) Date of Patent: Sep. 1, 2015

(54) RETAINERS FOR TRANSCATHETER HEART VALVE DELIVERY SYSTEMS

(75) Inventors: Huisun Wang, Maple Grove, MN (US); Valerie J. Glazier, Eden Prairie, MN (US); Alex Grafov, Eden Prairie, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 1005 days.

(21) Appl. No.: 13/180,720

(22) Filed: Jul. 12, 2011

(65) Prior Publication Data

US 2012/0078350 A1    Mar. 29, 2012

Related U.S. Application Data

(60) Provisional application No. 61/364,453, filed on Jul. 15, 2010.

(51) Int. Cl.
*A61F 2/24*   (2006.01)
*A61F 2/962*  (2013.01)
(Continued)

(52) U.S. Cl.
CPC .............. *A61F 2/2436* (2013.01); *A61F 2/962* (2013.01); *A61F 2/966* (2013.01); *A61F 2002/9522* (2013.01); *A61F 2002/9665* (2013.01)

(58) Field of Classification Search
CPC ........... A61F 2002/9505; A61F 2/2427; A61F 2/243; A61F 2/2433; A61F 2/2436; A61F 2/2439; A61F 2/962; A61F 2002/9511; A61F 2002/9522; A61F 2002/9665
USPC .................... 623/2.11, 1.11–1.12; 606/118
See application file for complete search history.

(56) References Cited

U.S. PATENT DOCUMENTS 5,733,325 A * 3/1998 Robinson et al. ............ 623/1.11
5,797,952 A * 8/1998 Klein ........................... 623/1.12

(Continued)

FOREIGN PATENT DOCUMENTS

DE   102004062296 A1   7/2006
WO       9620025 A1    7/1996

(Continued)

OTHER PUBLICATIONS

International Search Report and Written Opinion for Application No. PCt/US2011/001218 dated Nov. 11, 2011.

(Continued)

*Primary Examiner* — Julian W Woo
*Assistant Examiner* — Shaun L David
(74) *Attorney, Agent, or Firm* — Lerner, David, Littenberg, Krumholz & Mentlik, LLP

(57) ABSTRACT

A delivery device for an implantable medical device having at least one retention member at an end thereof includes a shaft extending in a longitudinal direction, an elongated sheath surrounding a longitudinal portion of the shaft, a compartment defined inside of the sheath and adapted to receive the medical device in an assembled condition, a retainer positioned at one end of the compartment, and at least one acceptance in the retainer adapted to receive the retention member of the medical device in the assembled condition. The sheath is slidable relative to the shaft in the longitudinal direction to uncover and deploy the medical device. The retainer may be rotatable relative to the shaft to reduce torsional forces in the medical device during delivery and deployment. The retainer may have at least one recess facing the compartment for receiving a strut at an end of a stent of the medical device.

19 Claims, 7 Drawing Sheets

(51) Int. Cl.
*A61F 2/966* (2013.01)
*A61F 2/95* (2013.01)

(56) References Cited

U.S. PATENT DOCUMENTS

| | | | |
|---|---|---|---|
| 6,214,036 B1* | 4/2001 | Letendre et al. | 623/1.11 |
| 6,623,518 B2 | 9/2003 | Thompson et al. | |
| 6,776,791 B1* | 8/2004 | Stallings et al. | 623/1.11 |
| 8,414,644 B2* | 4/2013 | Quadri et al. | 623/2.11 |
| 2002/0120323 A1* | 8/2002 | Thompson et al. | 623/1.11 |
| 2004/0087900 A1* | 5/2004 | Thompson et al. | 604/96.01 |
| 2004/0204749 A1* | 10/2004 | Gunderson | 623/1.12 |
| 2004/0236406 A1* | 11/2004 | Gregorich | 623/1.16 |
| 2004/0267348 A1* | 12/2004 | Gunderson et al. | 623/1.12 |
| 2005/0222662 A1* | 10/2005 | Thompson et al. | 623/1.11 |
| 2006/0100688 A1 | 5/2006 | Jordan et al. | |
| 2006/0111771 A1* | 5/2006 | Ton et al. | 623/1.15 |
| 2006/0259120 A1* | 11/2006 | Vongphakdy et al. | 623/1.11 |
| 2007/0027534 A1 | 2/2007 | Bergheim et al. | |
| 2007/0203561 A1 | 8/2007 | Forster et al. | |
| 2007/0293930 A1* | 12/2007 | Wang et al. | 623/1.11 |
| 2008/0114443 A1* | 5/2008 | Mitchell et al. | 623/1.13 |
| 2008/0221666 A1* | 9/2008 | Licata et al. | 623/1.22 |
| 2009/0281610 A1 | 11/2009 | Parker | |
| 2010/0131039 A1 | 5/2010 | Chau et al. | |
| 2010/0152834 A1* | 6/2010 | Hannes et al. | 623/1.15 |
| 2011/0077731 A1 | 3/2011 | Lee et al. | |
| 2011/0078350 A1 | 3/2011 | Carls | |
| 2011/0098805 A1* | 4/2011 | Dwork et al. | 623/2.11 |
| 2011/0172764 A1 | 7/2011 | Badhwar | |
| 2011/0264201 A1 | 10/2011 | Yeung et al. | |
| 2011/0264202 A1 | 10/2011 | Murray, III et al. | |
| 2011/0301685 A1 | 12/2011 | Kao | |
| 2012/0123528 A1 | 5/2012 | Knippel et al. | |

FOREIGN PATENT DOCUMENTS

| | | |
|---|---|---|
| WO | 9748343 A1 | 12/1997 |
| WO | 9965418 A1 | 12/1999 |
| WO | 2006124549 A1 | 11/2006 |
| WO | 2007002863 A2 | 1/2007 |
| WO | 2007134290 A2 | 11/2007 |
| WO | 2008031103 A2 | 3/2008 |
| WO | 2008097556 A1 | 8/2008 |
| WO | 2009062955 A1 | 5/2009 |
| WO | 2009/091509 A1 | 7/2009 |
| WO | 2009108942 A1 | 9/2009 |
| WO | 2010005524 A2 | 1/2010 |
| WO | 2011025945 A1 | 3/2011 |

OTHER PUBLICATIONS

International Search Report and Written Opinion for Application No. PCT/US2012/047283 dated Oct. 30, 2012.
International Search Report dated Feb. 2, 2012 for Application No. PCT/US2011/001446.
International Search Report for Application No. PCY/US2011/001596 dated May 8, 2012.
International Search Report and Written Opinion for Application No. PCT/US2013/047891 dated Dec. 4, 2013.
International Search Report and Written Opinion for Application No. PCT/US2013/048413 dated Dec. 4, 2013.

* cited by examiner

RETAINERS FOR TRANSCATHETER HEART VALVE DELIVERY SYSTEMS

CROSS-REFERENCE TO RELATED APPLICATIONS

This application claims the benefit of the filing date of U.S. Provisional Patent Application No. 61/364,453 filed Jul. 15, 2010, the disclosure of which is hereby incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which collapsible valves are mounted: a self-expanding stent and a balloon-expandable stent. To place a collapsible valve into a delivery apparatus and ultimately into a patient, the valve must first be collapsed or crimped to reduce its circumferential size.

When a collapsed valve has reached the desired implant site in the patient (e.g., at or near the annulus of the patient's heart valve that is to be replaced by the prosthetic valve), the prosthetic valve can be released from the delivery apparatus and re-expanded to full operating size.

Despite the various improvements that have been made to the collapsible prosthetic heart valve delivery process, conventional delivery devices, systems, and methods suffer from some shortcomings. For example, the self-expanding collapsible valve may be held in a catheter by stent retention members that are inserted into the retainer portion of the catheter. During deployment of the self-expanding valve into the desired area (e.g., the aortic valve annulus), the high frictional force produced during unsheathing of the valve may cause high axial forces to be applied directly to the two or three retention members, which may damage or deform the stent struts that support the retention members.

Furthermore, the delivery process may cause the stent to become twisted relative to the retainer portion of the catheter, which may make it difficult to release the valve because the stent retention members may catch on the retainer during deployment.

There therefore is a need for further improvements to the devices, systems, and methods for transcatheter delivery of collapsible prosthetic heart valves. Among other advantages, the present invention may address one or more of these shortcomings.

BRIEF SUMMARY OF THE INVENTION

A delivery device for an implantable medical device, a system for implantable medical device delivery, and a method of prosthetic valve delivery are disclosed.

A delivery device for an implantable medical device having at least one retention member at an end thereof includes a shaft extending in a longitudinal direction, an elongated sheath surrounding a longitudinal portion of the shaft, the sheath being slidable relative to the shaft in the longitudinal direction, a compartment defined inside of the sheath and adapted to receive the medical device in an assembled condition, a retainer positioned at one end of the compartment, the retainer including an inner piece and an outer piece mounted on the inner piece so as to be rotatable about the inner piece and constrained from movement relative to the inner piece in the longitudinal direction, and at least one acceptance in the retainer adapted to receive the retention member of the medical device in the assembled condition.

One of the outer piece and the inner piece may include a circumferentially extending groove and another of the outer piece and the inner piece may include an annular ring assembled in the groove and permitting the outer piece to rotate about the inner piece. The retainer may further include a support piece mounted on the inner piece and fixedly connected to the outer piece, whereby the outer piece and the support piece are rotatable together about the inner piece. The medical device may include a self-expanding stent having a plurality of struts and the outer piece may have a retention edge facing the compartment and at least one recess extending in the longitudinal direction from an open end at the retention edge to a closed end, the recess being adapted to receive one of the plurality of struts at an end of the stent in the assembled condition.

The acceptance may have a length in the longitudinal direction such that in the assembled condition the one of the plurality of struts contacts the closed end of the recess while the retention member is spaced from a closed end of the acceptance. The outer piece may have a retention edge facing the compartment and the acceptance may have a first region sized to receive the retention member, the acceptance including at least one protuberance defining a narrowed neck between the first region and the retention edge. The delivery device may also include a pin extending radially outward from the at least one acceptance, the pin being adapted to engage an aperture in the retention member, and an actuator coupled to the pin and adapted to move the pin in the longitudinal direction, thereby adjusting the longitudinal position of the retention member relative to the acceptance. The medical device may be a self-expanding collapsible prosthetic valve.

A system for implantable medical device delivery includes a delivery device including a shaft extending in a longitudinal direction, an elongated sheath surrounding a longitudinal portion of the shaft, the sheath being slidable relative to the shaft in the longitudinal direction, a compartment defined inside of the sheath, a retainer positioned at one end of the compartment, the retainer including an inner piece and an outer piece mounted on the inner piece so as to be rotatable about the inner piece and constrained from movement relative to the inner piece in the longitudinal direction, and at least one acceptance in the retainer. The system for implantable medical device delivery also includes an implantable medical device assembled in the compartment, the medical device having at least one retention member at an end thereof, the retention member being positioned in the acceptance.

One of the outer piece and the inner piece may include a circumferentially extending groove and another of the outer piece and the inner piece may include an annular ring assembled in the groove and permitting the outer piece to rotate about the inner piece. The retainer may further include a support piece mounted on the inner piece and fixedly connected to the outer piece, whereby the outer piece and the support piece are rotatable together about the inner piece. The medical device may include a self-expanding stent having a plurality of struts and the outer piece may have a retention edge facing the compartment and at least one recess extending in the longitudinal direction from an open end at the retention edge to a closed end, one of the plurality of struts at an end of the stent being assembled in the recess.

The acceptance may have a length in the longitudinal direction such that the one of the plurality of struts contacts the closed end of the recess while the retention member is spaced from a closed end of the acceptance. The outer piece may have a retention edge facing the compartment and the acceptance may have a first region sized to receive the retention member, the acceptance including at least one protuberance defining a narrowed neck between the first region and the retention edge. The system for implantable medical device delivery may also include a pin extending radially outward from the at least one acceptance and engaged in an aperture in the retention member, and an actuator coupled to the pin and adapted to move the pin in the longitudinal direction, thereby adjusting the longitudinal position of the retention member relative to the acceptance.

A delivery device for an implantable medical device having at least one retention member at an end thereof includes a shaft extending in a longitudinal direction, an elongated sheath surrounding a longitudinal portion of the shaft, the sheath being slidable relative to the shaft in the longitudinal direction, a compartment defined inside of the sheath and adapted to receive the medical device in an assembled condition, a retainer positioned at one end of the compartment, the retainer having a retention edge facing the compartment, and at least one acceptance in the retainer adapted to receive the retention member of the medical device in the assembled condition, the acceptance having a length in the longitudinal direction such that in the assembled condition the length of the acceptance is greater than a length of the retention member in the longitudinal direction.

The medical device may include a self-expanding stent having a plurality of struts and the retainer may have at least one recess extending in the longitudinal direction from an open end at the retention edge to a closed end, the recess being adapted to receive one of the plurality of struts at an end of the stent in the assembled condition. The acceptance may have a first region sized to receive the retention member, the acceptance including at least one protuberance defining a narrowed neck between the first region and the retention edge. The medical device may be a self-expanding collapsible prosthetic valve.

The delivery device may also include a pin extending radially outward from the at least one acceptance, the pin being adapted to engage an aperture in the retention member, and an actuator coupled to the pin and adapted to move the pin in the longitudinal direction, thereby adjusting the longitudinal position of the retention member relative to the acceptance. In the assembled condition, the one of the plurality of struts may contact the closed end of the recess while the retention member is spaced from a closed end of the acceptance. The acceptance may have a first region sized to receive the retention member, the acceptance including at least one protuberance defining a narrowed neck between the first region and the retention edge.

A method of prosthetic valve delivery includes providing a prosthetic valve having at least one retention member at an end thereof, mounting the valve in a compartment of a delivery device, the delivery device including a shaft, an elongated sheath surrounding a longitudinal portion of the shaft and slidable in longitudinal directions relative to the valve, a retainer positioned at one end of the compartment, and at least one acceptance in the retainer, the valve being mounted in the compartment with the retention member positioned in the acceptance, inserting the delivery device in a patient to position the valve at a target location, deploying the valve by sliding the sheath in a first one of the longitudinal directions relative to the valve, and adjusting the longitudinal position of the retention member relative to the acceptance during the deploying step.

The valve may include a self-expanding stent having a plurality of struts and the retainer includes a recess facing the compartment and extending longitudinally from an open end to a closed end, the valve being mounted in the compartment with one of the struts positioned in the recess. The method may further include forcing the one of the struts into engagement with the recess during the deploying step, such that a longitudinal force is not exerted on the retention member. The acceptance may include at least one protuberance defining a narrowed neck in the acceptance.

The method may further include resheathing the valve by sliding the sheath in a second one of the longitudinal directions relative to the valve opposite the first longitudinal direction, whereby an engagement of the retention member with the protuberance keeps the retention member positioned in the acceptance during the resheathing. The retainer may include a pin extending radially outward from the acceptance and engaged in an aperture in the retention member, and the delivery device includes an actuator coupled to the pin and adapted to move the pin in the longitudinal directions. The method may further include moving the actuator in at least one of the longitudinal directions to adjust the longitudinal position of the retention member relative to the acceptance.

A method of prosthetic valve delivery includes providing a prosthetic valve having at least one retention member at an end thereof and a self-expanding stent having a plurality of struts, mounting the valve in a compartment of a delivery device, the delivery device including a shaft, an elongated sheath surrounding a longitudinal portion of the shaft and slidable in longitudinal directions relative to the valve, a retainer positioned at one end of the compartment and having a recess facing the compartment and extending longitudinally from an open end to a closed end, and at least one acceptance in the retainer, the valve being mounted in the compartment with the retention member positioned in the acceptance and with one of the struts positioned in the recess, inserting the delivery device in a patient to position the valve at a target location, and deploying the valve by sliding the sheath in a first one of the longitudinal directions relative to the valve, the deploying step forcing the one of the struts into engagement with the recess such that a longitudinal force is not exerted on the retention member.

The acceptance may include at least one protuberance defining a narrowed neck in the acceptance. The method may further include resheathing the valve by sliding the sheath in a second one of the longitudinal directions relative to the valve opposite the first longitudinal direction, whereby an engagement of the retention member with the protuberance keeps the retention member positioned in the acceptance during the resheathing.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a surgeon using the disclosed delivery devices. "Proximal" is to be understood as relatively close to the surgeon and "distal" is to be understood as relatively farther away from the surgeon.

Figure 1A:
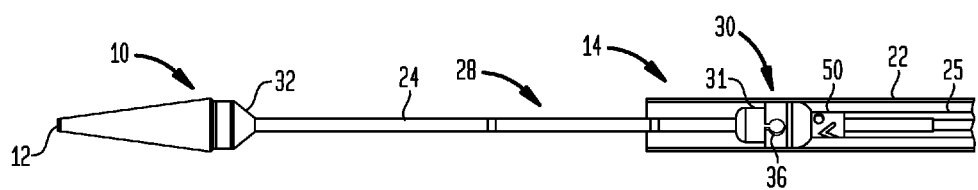
FIG. 1A is a side view of a transfemoral delivery device for a collapsible prosthetic heart valve.

Referring now to FIG. 1A to illustrate the structure and function of the present invention, a first embodiment of a delivery device 10 has a distal tip 12 and a catheter assembly 14 extending from the distal tip 12 to a proximal end (not shown) that includes a handle (not shown) for a user to control the delivery device 10. The delivery device 10 is an exemplary transfemoral delivery device for a collapsible prosthetic heart valve.

Although the delivery device 10 is a transfemoral delivery device, the inventive retainers shown and described in this application may be configured to be used with a transapical delivery device (e.g., the device 10' shown in FIGS. 2A and 2B) or other types of tube-like delivery devices for collapsible stents.

The catheter assembly 14 includes a sheath 22 extending from the handle towards the distal tip 12, a hollow inner shaft 24 located inside of the sheath 22 and extending from the handle to the distal tip 12, and a valve receiving compartment 28 configured to receive a prosthetic valve for delivery inside of a patient.

The valve receiving compartment 28 is configured to receive a collapsible prosthetic heart valve (e.g., stent portions of collapsible prosthetic valves are shown in FIGS. 5A, 6A, and 7-10). The valve receiving compartment 28 includes a retainer 30 located inside the sheath 22, a proximal conical end 31 adjacent the retainer 30, and a distal conical end 32 spaced from the retainer 30. The conical end 32 is joined to the inner shaft 24 at one end of the valve receiving compartment 28, and the conical end 31 and the retainer 30 are joined to a stiffening member 25 mounted on the inner shaft 24 at the other end of the valve receiving compartment 28. Preferably, the inner shaft 24 and the stiffening member 25 have the same internal diameter, adapted to receive a guide wire (not shown). Alternatively, in any of the delivery device embodiments described herein, the inner shaft 24 and the stiffening member 25 may be a single unitary shaft. For delivery into a patient, a collapsible valve is loaded into the valve receiving compartment 28 around the inner shaft 24 and between conical ends 31 and 32, and the stent portion of the valve is coupled to the retainer 30.

Figure 1B:
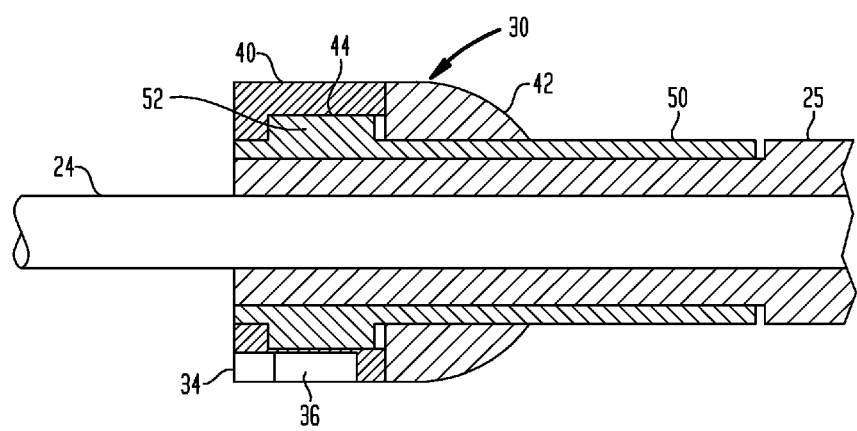
FIG. 1B is a longitudinal cross-section of the retainer of the delivery device depicted in FIG. 1A, shown without the proximal conical end and the distal sheath.

Referring now to FIG. 1B, the retainer 30 includes an outer piece 40, a support piece 42 located adjacent to the outer piece 40, and an inner piece 50 that is coupled to the outer piece 40 so as to be rotatable relative thereto. The outer piece 40 defines one or more acceptances 36, each acceptance 36 being located at the retention edge 34 of the outer piece 40 and configured to receive a corresponding retention member of a stent portion of the collapsible valve (see, for example, retention member 4 in FIG. 6A). Each acceptance 36 preferably has a similar shape and a slightly larger size than a conventional stent retention member so as to capture same readily, but with only a small amount of relief therebetween. Forming acceptances 36 with an appropriate shape and size prevents longitudinal movement of the valve within the valve receiving compartment 28, such as during deployment or resheathing procedures.

In the embodiment shown in FIG. 1B, the outer piece 40 and the support piece 42 are attached together (e.g., via welding or any other known joining technique) so that they are rotatable together relative to the inner piece 50. In other embodiments (such as the embodiment shown in FIG. 4), the outer piece and the support piece may be rotatable relative to each other. For example, the support piece may be attached to the inner piece, such that the outer piece may rotate relative to both the support piece and the inner piece.

The inner piece 50 includes an annular ring 52 that is adapted to fit into a corresponding circumferential groove 44 defined in the outer piece 40. The ring 52 and the groove 44 are configured such that the outer piece 40 and the support piece 42 can freely rotate about the inner piece 50 but not slide longitudinally by any significant amount relative to the inner piece. In the embodiments shown, a small amount of longitudinal movement is permitted between the outer piece 40 and the inner piece 50 so as to minimize frictional braking forces between these elements, but the ring 52 and the groove 44 retain the outer piece 40 and the support piece 42 on the inner piece 50 during use of the retainer 30.

To load the delivery device 10 with a collapsible prosthetic valve, a user attaches the stent portion of the prosthetic valve to the outer piece 40 and compresses or crimps the valve until it fits inside the sheath 22, which holds the valve in a compressed state until the user decides to deploy the valve. When the valve is later deployed by unsheathing, the stent self-expands and is ultimately disengaged from the outer piece 40.

If the valve has not been fully deployed, i.e., if a portion of the valve remains in a collapsed state beneath sheath 22, the valve may be resheathed by sliding the sheath back over the portion of the stent that has expanded, thereby recollapsing the expanded portion of the stent.

Regardless of whether a valve is to be delivered transapically or transfemorally into a patient to replace a native valve (e.g., the patient's aortic valve), the stent portion of the valve preferably is attached to the retainer by retention members protruding from the end of the stent that is opposite the end at which the valve is located (i.e., the retention members protrude from the aortic side of the stent). Preferably, the retention members are positioned at the end of the valve that is to be deployed last, i.e., the end of the valve that will be covered by the sheath the longest.

For example, in a transfemoral prosthetic aortic valve delivery device (e.g., the device 10 shown in FIG. 1A), the retention edge 34 of the outer piece 40 is located at the distal end of the outer piece, and the sheath 22 is moved in a proximal direction to unsheathe and deploy the valve, with the distal end of the valve unsheathed first.

The retention edge 34 of the outer piece 40 may have a chamfered outer edge, which may help reduce frictional forces acting between the sheath 22 and the outer piece 40 during unsheathing and resheathing of a stent. The retention edge of any of the retainer embodiments disclosed herein may have chamfered outer edges.

When the delivery device 10 is being used to deliver a collapsible valve into a patient, the ability of the outer piece 40 to freely rotate about the inner piece 50 may allow the outer piece 40 to move to a circumferential position that minimizes the twisting forces experienced by a stent that is coupled to the acceptances 36.

For example, as the delivery device 10 is advanced into a patient, such as through the femoral artery towards the aorta, the stent portion of the prosthetic valve may become twisted about its longitudinal axis relative to the retainer 30 due to the maneuvering of the delivery device through the vasculature, thereby applying torsional stress both to the stent and to the stent's retention members that are coupled to the acceptances 36. However, as the outer piece 40 is free to rotate, these torsional stresses will cause the outer piece to rotate relative to the inner piece 50 and the sheath 22, releasing the torsional forces acting on the stent and its retention members.

Figure 2A:
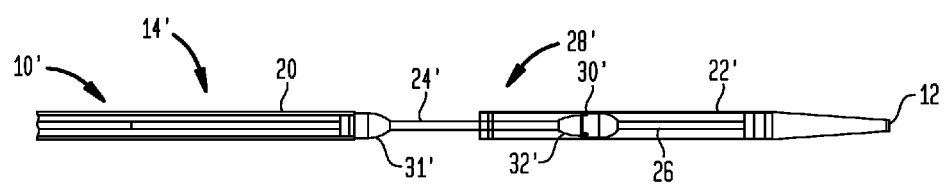
FIG. 2A is a side view of a transapical delivery device for a collapsible prosthetic heart valve.

Referring to FIG. 2A, a second embodiment of a delivery device 10' has a distal tip 12 and a catheter assembly 14' extending from the distal tip 12 to a proximal end (not shown) that includes a handle (not shown) for a user to control the delivery device 10'. The delivery device 10' is an exemplary transapical delivery device for a collapsible prosthetic heart valve.

The catheter assembly 14' includes a proximal sheath extending from the handle towards the distal tip 12, a distal sheath 22' extending from the distal tip 12 towards the handle, a hollow tube 26 that extends slidably from the proximal end through the proximal sheath 20 and attaches to the distal sheath 22' at the distal tip 12 of the delivery device 10', and a valve receiving compartment 28' configured to receive a prosthetic valve for delivery inside of a patient.

The valve receiving compartment 28' is configured to receive a collapsible prosthetic heart valve. The valve receiving compartment 28' includes a proximal conical end 31' at the distal end of the proximal sheath 20, a distal conical end 32' spaced from the proximal conical end, and a retainer 30' located adjacent the distal conical end 32' and inside the distal sheath 22'. A hollow inner shaft 24' is connected at one end to the proximal conical end 31' and at the other end to the distal conical end 32', and slidably receives the hollow tube 26 therethrough. For delivery into a patient, a collapsible valve is loaded into the valve receiving compartment 28' around the inner shaft 24' and between the conical ends 31' and 32', and the stent portion of the valve is coupled to the retainer 30'.

Figure 2B:
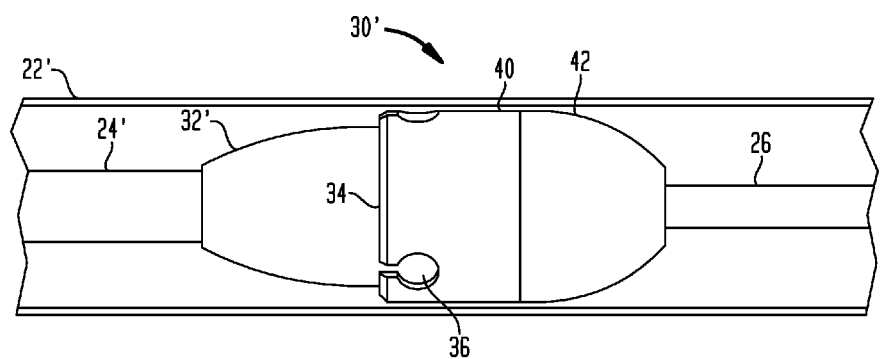
FIG. 2B is a side view of the retainer of the delivery device of FIG. 2A.

Referring now to FIG. 2B, the retainer 30' includes an outer piece 40, a support piece 42 located adjacent to the outer piece 40, and an inner piece (not shown, but attached to the outside of the inner shaft 24') that is coupled to the outer piece 40 so as to be rotatable relative thereto. The outer piece 40 defines one or more acceptances 36, each acceptance 36 being located at the retention edge 34 of the outer piece 40 and configured to receive a corresponding retention member of the stent portion of a collapsible prosthetic valve. Each acceptance 36 preferably has a similar shape and a slightly larger size than a conventional stent retention member so as to capture same readily, but with only a small amount of relief therebetween.

In a transapical prosthetic aortic valve delivery device (e.g., the device 10' shown in FIGS. 2A and 2B), the retention edge 34 is located at the proximal end of the outer piece 40, and the distal sheath 22' is moved in a distal direction to unsheathe and deploy the valve, with the proximal end of the valve unsheathed first.

Figure 2C:
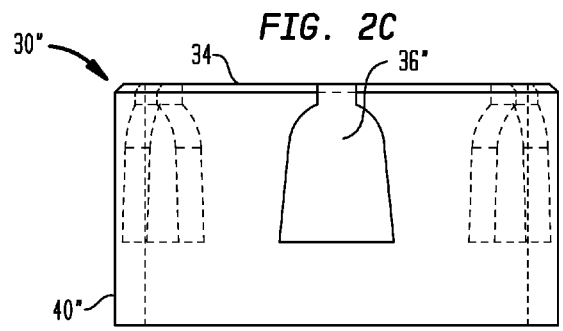
FIG. 2C is an enlarged side view of another embodiment of a retainer suitable for use in the delivery device of FIG. 2A.

Referring now to FIG. 2C, a retainer 30" suitable for use in the delivery device 10 shown in FIG. 1A or the delivery device 10' shown in FIG. 2A includes an alternate outer piece 40" having one or more acceptances 36", each acceptance 36" being located at the retention edge 34 of the outer piece 40" and configured to receive a corresponding retention member of the stent portion of a collapsible prosthetic valve.

Compared to the acceptances 36 shown in FIGS. 1A and 2B, each acceptance 36" shown in FIG. 2C narrows as it approaches the retention edge 34, such that the end of the acceptance 36" that is farthest away from the retention edge 34 is wider than the portion of the acceptance 36" that is closer to the retention edge 34. The tapered shape of the acceptances 36" shown in FIG. 2C may allow a user to more easily load the retention members of a stent into the retainer 30", as compared to the shape of the acceptances 36 shown in FIGS. 1A and 2B. Acceptances 36" having a tapered shape may be used in any of the retainer embodiments disclosed herein.

Figure 3:
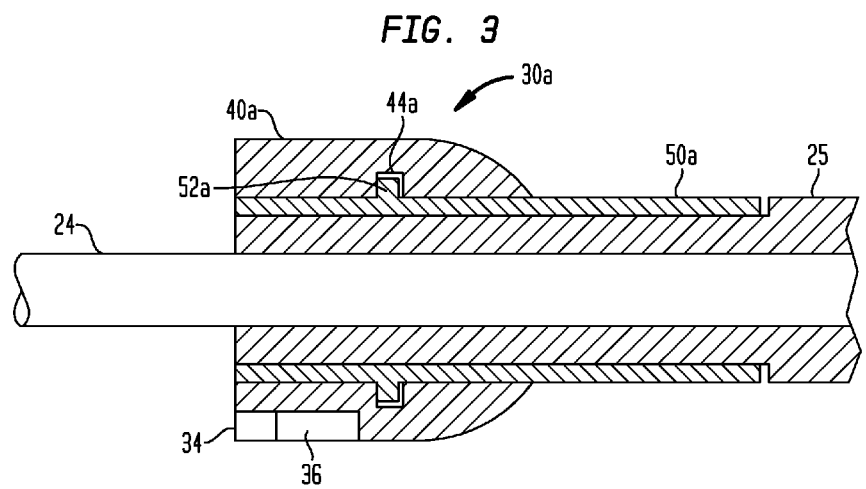
FIG. 3 is a longitudinal cross-section of another embodiment of a retainer suitable for use in the delivery device of FIG. 1A.

Referring now to FIG. 3, another embodiment of a retainer 30a suitable for use in the delivery device 10 shown in FIG. 1A includes an outer piece 40a that is coupled to an inner piece 50a so as to be rotatable relative to same. The outer piece 40a defines one or more acceptances 36, each acceptance 36 being located at the retention edge 34 of the outer piece 40a and configured to receive a corresponding retention member of the stent portion of a collapsible valve. The retainer 30a is attached to a stiffening member 25 mounted on the hollow inner shaft 24.

The outer piece 40a in the retainer 30a has a shape that resembles the combined shape of the outer piece 40 and the support piece 42 of the retainer 30. The inner piece 50a includes an annular ring 52a that is adapted to fit into a corresponding circumferential groove 44a defined in the outer piece 40a. Similar to the retainer 30 shown in FIG. 1B, the ring and the groove construction enables the outer piece 40a to freely rotate about the inner piece 50a but not slide longitudinally by any significant amount relative to the inner piece 50a.

Figure 4:
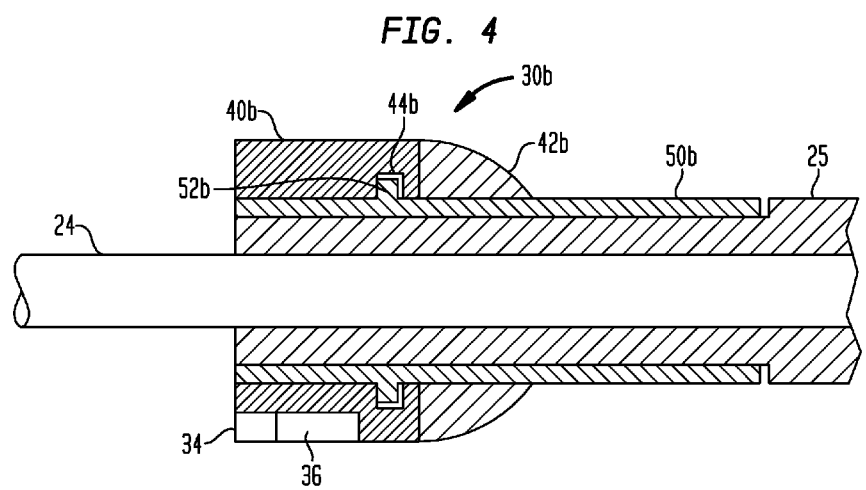
FIG. 4 is a longitudinal cross-section of another embodiment of a retainer suitable for use in the delivery device of FIG. 1A.

Referring now to FIG. 4, a further embodiment of a retainer 30b suitable for use in the delivery device 10 shown in FIG. 1A includes an inner piece 50b, an outer piece 40b rotatably coupled to the inner piece, and a support piece 42b located adjacent to the outer piece 40b and fixedly coupled to the inner piece. As a result, as the outer piece 40b rotates relative to the inner piece 50b, it will also rotate relative to the support piece 42b. The outer piece 40b includes one or more acceptances 36, each of which is located at the retention edge 34 of the outer piece and configured to receive a corresponding retention member of the stent portion of a collapsible valve. The retainer 30b is attached to a stiffening member 25 mounted on the hollow inner shaft 24.

The inner piece 50b includes an annular ring 52b that is adapted to fit into a corresponding circumferential groove 44b defined in the outer piece 40b. Similar to the retainer 30 shown in FIG. 1B, the ring 52b and the groove 44b are configured to enable the outer piece 40b to freely rotate about the inner piece 50b but not slide longitudinally by any significant amount relative to the inner piece.

Figure 5A:
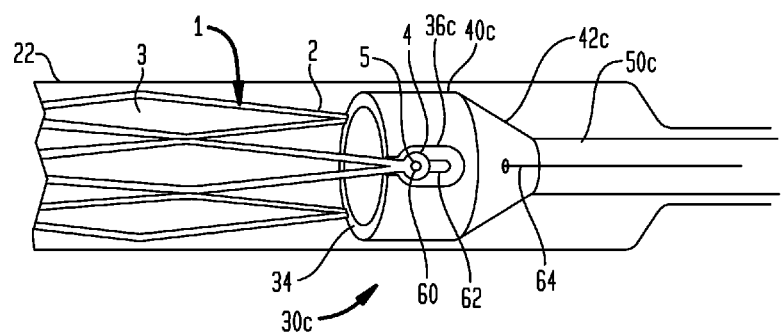
FIG. 5A is a side perspective view of another embodiment of a retainer suitable for use in the delivery device of FIG. 1A, shown holding a stent in a compressed state inside a distal sheath.
Figure 5B:
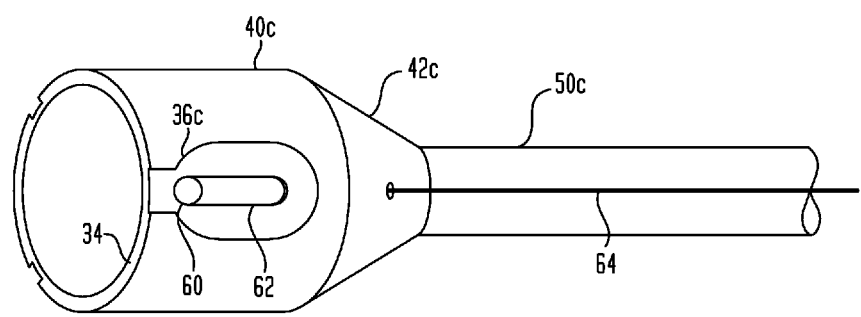
FIG. 5B is an enlarged side perspective view of a portion of the retainer depicted in FIG. 5A.

Referring now to FIGS. 5A and 5B, yet another embodiment of a retainer 30c suitable for use in the delivery device 10 shown in FIG. 1A includes an outer piece 40c, a support piece 42c located adjacent to the outer piece 40c, and an inner piece 50c that is rotatably coupled to the outer piece 40c. The support piece 42c can either be attached to the outer piece 40c so as to be rotatable relative to the inner piece 50c, or fixedly attached to the inner piece 50c so that there is relative rotational movement between the outer piece 40c and the support piece 42c. The outer piece 40c includes one or more acceptances 36c, each being located at the retention edge 34 of the outer piece 40c.

Similar to the retainer 30 shown in FIG. 1B, the retainer 30c includes a ring and groove configuration (not shown) that permits the outer piece 40c to freely rotate about the inner piece 50c but prevents significant longitudinal movement between the two.

The stent portion 1 of a collapsible valve is shown coupled to the retainer 30c. The stent portion 1 includes a plurality of stent struts 2 that define cells 3 therebetween. At least one retention member 4 extends from an end of the stent portion 1. Each retention member 4 includes an aperture 5. As mentioned above with respect to the retainer 30, regardless of whether a valve is to be delivered transapically or transfemorally into a patient to replace a native valve (e.g., the patient's aortic valve), the stent 1 containing the valve preferably is attached to the retainer 30c by retention members 4 protruding from the end of the stent 1 that is opposite the end at which the valve is located (i.e., the retention members 4 protrude from the aortic side of the stent 1).

In the retainer 30c, the position of retention members 4 in acceptances 36c is independently longitudinally adjustable by the user. That is, one or more acceptances 36c include a pin 60 that is manually slidable in the acceptance in the longitudinal direction of the stent 1. Preferably, each of the acceptances 36c includes such a slidable pin 60. Each pin 60 is coupled to an actuator wire 64 that may be independently pushed or pulled by a user to slide the pin along a longitudinal slot 62. The retention members 4 of the stent 1 are coupled to the retainer 30c by inserting same into a corresponding acceptance 36c with the pin 60 thereof inserted through the aperture 5 of the retention member. Thus, by pulling the corresponding actuator wire 64 proximally or pushing the wire distally, a user can adjust the longitudinal position of the pin 60 of each acceptance 36c, and with it, the longitudinal position of the corresponding retention member 4.

When the delivery device 10 is being used to deliver a collapsible valve into a patient, the valve may become cocked at an angle relative to the retainer 30c and the acceptances 36c thereof, and as a result, may not readily release therefrom. The ability to independently adjust the longitudinal position of each retention member 4 relative to the retainer 30c may allow the valve to be straightened to facilitate its release from the delivery device 10.

For example, as the delivery device 10 is advanced into a patient, such as through the femoral artery towards the aorta, the stent portion of the prosthetic valve may become twisted about its longitudinal axis relative to the retainer 30c due to the maneuvering of the delivery device through the vasculature, thereby applying torsional stress both to the stent and to the stent's retention members that are coupled to the acceptances 36c. However, as the outer piece 40c is free to rotate, these torsional stresses will cause the outer piece to rotate relative to the inner piece 50c and the sheath 22, releasing the torsional forces acting on the stent and its retention members. If the user detects stress building up in the stent 1 or a misalignment of the stent 1 relative to the retainer 30c, potentially preventing the valve from being fully deployed or damaging the retention members 4, the user may independently adjust the longitudinal position of one or more retention members 4 relative to the retainer 30c and the acceptances 36c thereof, realigning the stent and enabling continued release of the valve.

Although the retainer 30c having the capability to independently longitudinally adjust the position of retention members 4 in the acceptances 36c is shown and described with reference to the rotatable retainer embodiments shown in FIGS. 1A through 4, the capability to independently longitudinally adjust the position of retention members 4 in the acceptances 36c may be incorporated into the embodiments shown in FIGS. 6A through 10 that include the feature wherein the length of the acceptances are greater than a length of the respective retention members in the longitudinal direction.

Figure 6A:
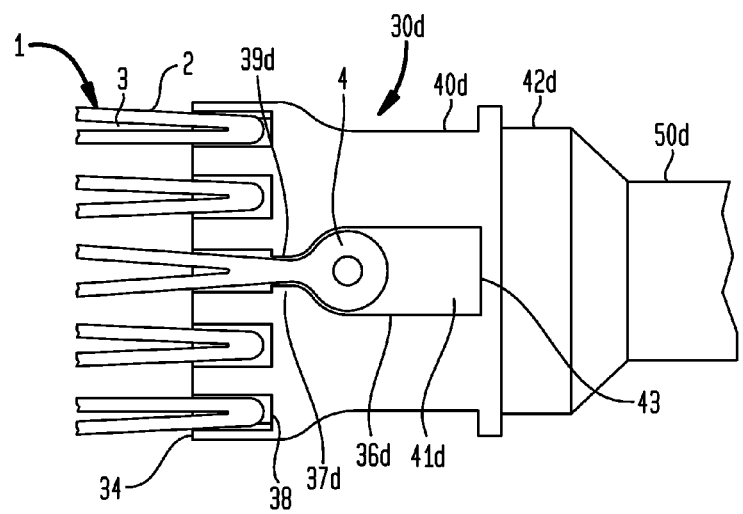
FIG. 6A is a side view of another embodiment of a retainer suitable for use in the delivery device of FIGS. 1A and 2A, shown holding a stent.
Figure 6B:
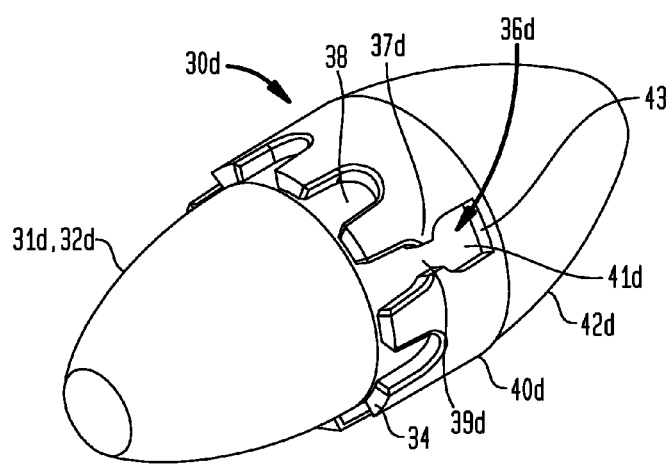
FIG. 6B is a perspective view of the retainer depicted in FIG. 6A, shown with a retainer cone.
Figure 6C:
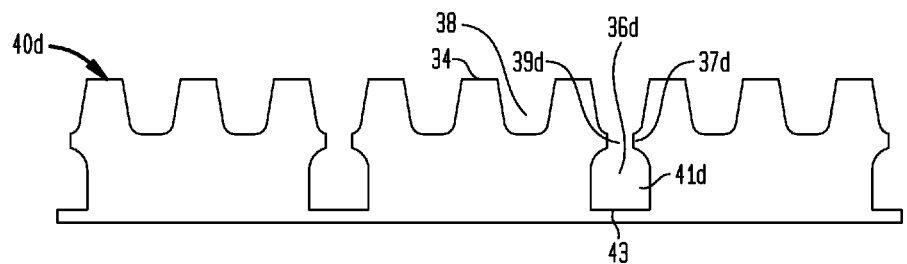
FIG. 6C is a developed view of the retainer depicted in FIG. 6B.

Referring now to FIGS. 6A-6C, a still further embodiment of a retainer 30d suitable for use in the delivery devices 10 and 10' shown in FIGS. 1A and 2A includes an inner piece 50d, an outer piece 40d that is rotatably coupled to the inner piece, and a support piece 42d coupled to the inner piece adjacent to the outer piece 40d. The support piece 42d can either be attached to the outer piece 40d so as to be rotatable relative to the inner piece 50d, or fixedly attached to the inner piece 50d so that there may be relative rotational movement between the outer piece 40d and the support piece 42d. The ability of the outer piece 40d to freely rotate relative to the inner piece 50d may provide the beneficial stent stress-reduction effects discussed above with respect to the embodiments of FIGS. 1-5.

Although the outer piece 40d is described herein as rotatably coupled to the inner piece 50d, in some embodiments, the outer piece 40d may be fixed to the inner piece 50d. The other features of the retainer 30d (e.g., the recesses 38) may be included in embodiments in which the outer piece 40d is either fixed or rotatable relative to the inner piece 50d. Similarly, the outer pieces shown in FIGS. 7-10 may be either fixed or rotatable relative to the corresponding inner pieces shown in those figures.

In a transfemoral delivery device such as the device 10 shown in FIG. 1A, the retainer 30d may be located adjacent to a proximal conical end 31d that is suitable for coupling to the inner shaft 24 of the delivery device. On the other hand, in a transapical delivery device such as the device 10' shown in FIG. 2A, the retainer 30d may be located adjacent to a distal conical end 32d that is suitable for coupling to the inner shaft 24' of the delivery device.

The outer piece 40d includes one or more acceptances 36d, each extending from the retention edge 34 of the outer piece 40d and configured to receive a corresponding retention member 4 of the stent portion of a collapsible prosthetic valve. Each acceptance 36d has an elongated shape, with protuberances 37d projecting towards one another to define a narrowed neck 39d that limits the longitudinal movement of a corresponding retention member 4 toward the retention edge 34. Neck 39d is positioned in acceptance 36d so as to define a pocket 41d spaced from retention edge 34. As can be seen in FIG. 6A, pocket 41d has a length in the longitudinal direction that is substantially larger than the size of the retention member 4.

Although three acceptances 36d are shown in the embodiment of FIG. 6C, the retainer 30d (and all of the other retainers disclosed herein) may have any number of acceptances, including for example, one, two, four, six, or eight acceptances. Further, each acceptance 36d (and all of the other acceptances disclosed herein) may have only a single protuberance 37d defining the neck 39d, or any number of protuberances greater than two. Although three retention members 4 are described as being engaged in the three respective acceptances 36d in this embodiment (and in the other embodiments described herein), the retainers described herein may be used with stents 1 having any number of retention members 4, including for example, one, two, four, six, or eight retention members.

The outer piece 40d further includes one or more recesses 38 extending inwardly from the retention edge 34 and configured to receive the V-shaped junction formed by the struts 2 at the end of the stent 1. The recesses 38 provide a limit to the longitudinal movement of a corresponding stent strut 2 relative to the retention edge 34. Furthermore, the recesses 38 fix the circumferential positions of the stent struts 2, preventing them from overlapping with one another and becoming otherwise entangled during the delivery and deployment of the prosthetic valve.

With a prosthetic valve assembled to the retainer 30d, as shown in FIG. 6A, the retention members 4 will be spaced from the end wall 43 of the pocket 41d. However, should any longitudinal force develop tending to push the prosthetic valve against the retainer 30d, the engagement of the stent struts 2 in the recesses 38 will prevent the longitudinal movement of the prosthetic valve relative to the retainer. As a result, the retention members 4 will remain spaced from the end walls 43 of the pockets 41d, and the compressive force between the stent 1 of the prosthetic valve and the retainer 30d will not be localized at the retention members, but rather will be distributed substantially uniformly around the circumference of the stent through stent struts 2. In consideration of the foregoing, it will be appreciated that the recesses 38 may be generally U-shaped as shown in FIG. 6C or may have any other shape that can receive a corresponding stent strut 2 and serve the purposes just described.

Similar to the retainer 30 shown in FIG. 1B, the retainer 30d includes an annular ring and groove configuration that permits the outer piece 40d to freely rotate about the inner piece 50d but prevents the outer piece from moving longitudinally relative to the inner piece.

During unsheathing of the stent 1 to deploy a collapsible valve into a desired location in a patient, the recesses 38 of the retainer 30d may direct the forces acting between the retainer and the stent onto the stent struts 2 that do not support the retention members 4 as described above, rather than onto the retention members 4 themselves. As a result, these forces are more evenly distributed around the circumference of the stent 1. This can prevent the retention members 4 or the stent struts 2 that support the retention members 4 from being damaged or deformed.

For example, unsheathing of the prosthetic valve will produce frictional forces between the sheath 22 or 22' (see FIGS. 1A and 2A) and the stent 1 that will either push or pull the stent 1 longitudinally against the retainer 30d. This longitudinal force will force the stent struts 2 into engagement with the bottoms of the recesses 38, while the retention members 4 remain spaced from the ends 43 of the pockets 41d, thereby preventing the application of a pushing force on the retention members.

During resheathing of the prosthetic valve, for example, when a user decides that the positioning of the valve in the patient needs to be adjusted, frictional forces will be produced between the sheath 22 or 22' and the stent 1 that will tend to push or pull the stent 1 out of engagement with the retainer 30d. In such an event, the retention members 4 are prevented from moving further away from the ends 43 of the pockets 41d by the protuberances 37.

Figure 7:
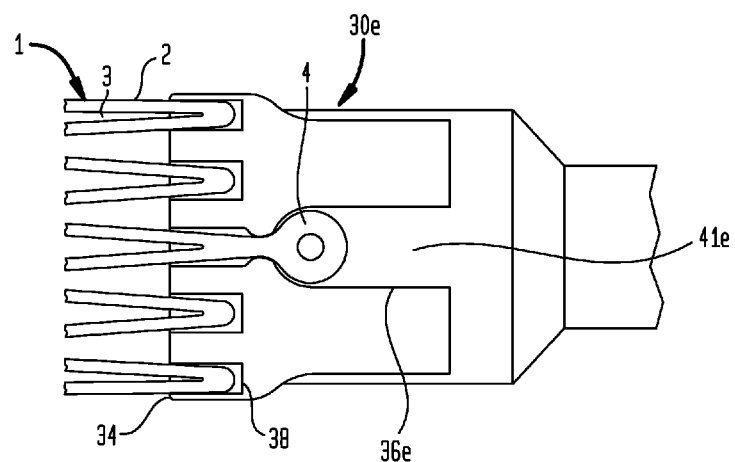
FIG. 7 is a side view of another embodiment of a retainer suitable for use in the delivery device of FIGS. 1A and 2A, shown holding a stent.

Yet another embodiment of a retainer 30e is shown in FIG. 7. The retainer 30e is suitable for use in the delivery devices 10 and 10' shown in FIGS. 1A and 2A, respectively. The retainer 30e is substantially the same as the retainer 30d described above. However, rather than having an end wall at the end of the pocket 41e remote from the retainer edge 34, such as the end wall 43 of the retainer 30d, the pockets 41e have an open end. It will be appreciated from the description above that the retention members 4 do not contact the end wall 43 of the retainer 30d during use of the deployment device to deploy or resheathe a prosthetic valve. Accordingly, the end wall 43 is not necessary and has been eliminated from the retainer 30e.

Figure 8:
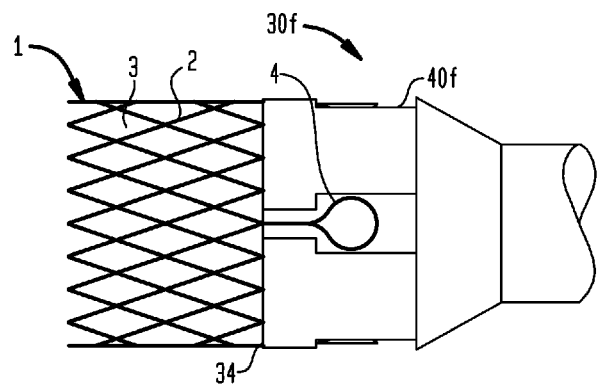
FIG. 8 is a side view of another embodiment of a retainer suitable for use in the delivery device of FIGS. 1A and 2A, shown holding a stent.

FIG. 8 illustrates yet a further embodiment of a retainer 30f suitable for use in the delivery devices 10 and 10' shown in FIGS. 1A and 2A, respectively. The retainer 30f is substantially similar to the retainer 30e described above, except for the elimination of the recesses 38 extending inwardly from the retention edge 34. Thus, in the retainer 30f, the retention edge 34 of the outer piece 40f provides a limit to the longitudinal movement of the stent struts 2 during the unsheathing or deployment of the prosthetic valve into a patient. However, as the retention edge 34 does not capture the stent struts 2 individually, the retainer 30f can not prevent the stent struts from overlapping with one another and becoming otherwise entangled during the use of the delivery device to deliver and deploy the prosthetic valve.

Figure 9:
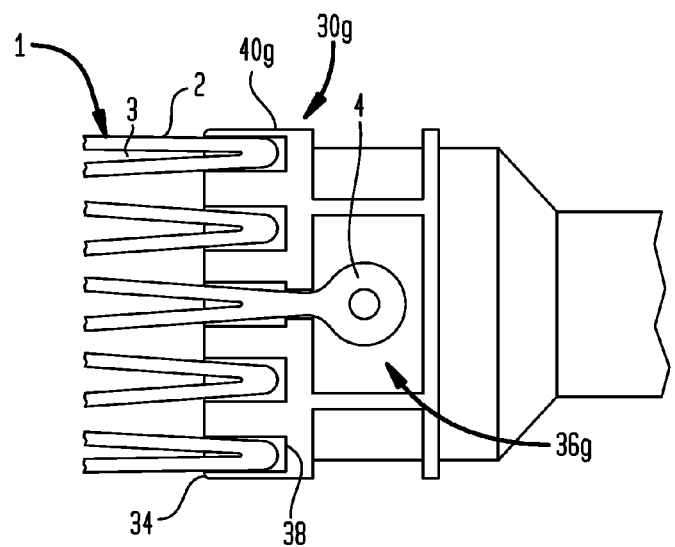
FIG. 9 is a side view of another embodiment of a retainer suitable for use in the delivery device of FIGS. 1A and 2A, shown holding a stent.

Still another embodiment of a retainer 30g is shown in FIG. 9. The retainer 30g is suitable for use in the delivery devices 10 and 10' shown in FIGS. 1A and 2A, respectively. The retainer 30g is substantially similar to the retainers 30d and 30e described above, but differs in the configuration of the outer piece 40g, and in particular, in the configuration of the acceptances 36g. Rather than having acceptances that fit closely to the retention members 4 in the circumferential direction but which have excess free space in the longitudinal direction as with the acceptances 36d and 36e, the acceptances 36g are oversized in both the longitudinal direction and in the circumferential direction. In that regard, the acceptances 36g may be oversized relative to the retention members 4 in the circumferential direction by any amount, such as, for example, 1.5, 3, and 4 times the dimension of the retention member 4 in the circumferential direction. A circumferential dimension that is at least about two times the corresponding dimension of the retention members 4 is preferred. The large oversize of acceptances 36g facilitates the assembly of the stent portion of a prosthetic valve within the valve receiving compartment 28 or 28' and may facilitate the deployment of the prosthetic valve by minimizing the possibility that the retention members 4 will fail to be released by the acceptances.

Figure 10:
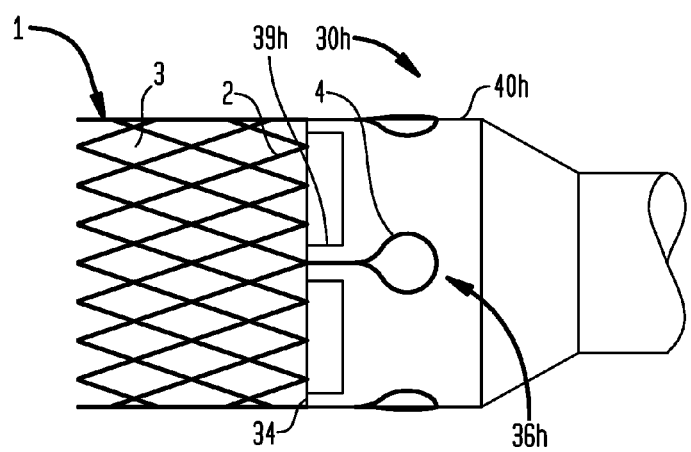
FIG. 10 is a side view of another embodiment of a retainer suitable for use in the delivery device of FIGS. 1A and 2A, shown holding a stent.

Another embodiment of a retainer 30h suitable for use in the delivery devices 10 and 10' is shown in FIG. 10. The retainer 30h is similar to the retainer 30f described above, but combines features of that retainer with features of the retainer 30g also described above. That is, the retainer 30h has a retention edge 34 devoid of the recesses 38 extending inwardly therefrom, as with the retainer 30f. Accordingly, the retention edge 34 of the outer piece 40h limits the longitudinal movement of the stent struts 2 during the unsheathing or deployment of a prosthetic valve. However, rather than having acceptances that fit closely to retention members 4 in the circumferential direction as in retainer 30f, retainer 30h has a single acceptance region 36h that essentially eliminates any structure that would reside between the retention members 4 when the prosthetic valve is assembled to the retainer. Hence, in the retainer 30h, the only structures that fix the position of the prosthetic valve relative to the retainer in the circumferential direction are the necks 39h that extend from the retention edge 34 to the acceptance region 36h. Nonetheless, the engagement of the stent struts 2 with the retention edge 34 and the engagement of the retention members 4 with the necks 39h substantially prevent the longitudinal movement of the prosthetic valve relative to the retainer 30h.

Although the various retainer embodiments have been described here in connection with retaining for deployment a prosthetic valve having a collapsible stent structure, all of the retainer embodiments may be used for other purposes. In particular, the various embodiments of retainers may be used to retain conventional collapsible stents that do not contain a valve.

Although the invention herein has been described with reference to particular embodiments in which the annulus end of a prosthetic valve is deployed first, it is to be understood that the invention contemplates embodiments in which the aortic end of a valve is deployed first. In such embodiments (not shown), retention members may protrude from the annulus end of the stent portion of the valve for engagement with a retainer of the delivery device, such that the aortic end of the stent is remote from the retainer and may be unsheathed first. In still other embodiments (not shown), retention members may protrude from both the aortic and the annulus ends of the stent portion of the valve for engagement with a retainer.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for an implantable medical device having at least one retention member at an end thereof, the delivery device comprising:
a shaft extending in a longitudinal direction;
an elongated sheath surrounding a longitudinal portion of the shaft, the sheath being slidable relative to the shaft in the longitudinal direction;
a compartment defined inside of the sheath and adapted to receive the medical device in an assembled condition;
a retainer positioned at one end of the compartment, the retainer including an inner piece and an outer piece mounted on the inner piece so as to be rotatable about the inner piece and constrained from movement relative to the inner piece in the longitudinal direction; and
at least one acceptance in the retainer adapted to receive the retention member of the medical device in the assembled condition,
wherein the outer piece has a retention edge facing the compartment and the acceptance has a first region sized to receive the retention member, the acceptance including at least one protuberance defining a narrowed neck between the first region and the retention edge.

2. The delivery device of claim 1, wherein one of the outer piece and the inner piece includes a circumferentially extending groove and another of the outer piece and the inner piece includes an annular ring assembled in the groove and permitting the outer piece to rotate about the inner piece.

3. The delivery device of claim 2, wherein the retainer further includes a support piece mounted on the inner piece and fixedly connected to the outer piece, whereby the outer piece and the support piece are rotatable together about the inner piece.

4. The delivery device of claim 1, wherein the medical device includes a self-expanding stent having a plurality of struts and the outer piece has a retention edge facing the compartment and at least one recess extending in the longitudinal direction from an open end at the retention edge to a closed end, the recess being adapted to receive one of the plurality of struts at an end of the stent in the assembled condition.

5. The delivery device of claim 4, wherein the acceptance has a length in the longitudinal direction such that in the assembled condition the one of the plurality of struts contacts the closed end of the recess while the retention member is spaced from a closed end of the acceptance.

6. The delivery device of claim 1, further comprising:
a pin extending radially outward from the at least one acceptance, the pin being adapted to engage an aperture in the retention member; and
an actuator coupled to the pin and adapted to move the pin in the longitudinal direction, thereby adjusting the longitudinal position of the retention member relative to the acceptance.

7. The delivery device of claim 1, wherein the medical device is a self-expanding collapsible prosthetic valve.

8. A system for implantable medical device delivery, the system comprising:
a delivery device including
a shaft extending in a longitudinal direction;
an elongated sheath surrounding a longitudinal portion of the shaft, the sheath being slidable relative to the shaft in the longitudinal direction;
a compartment defined inside of the sheath;
a retainer positioned at one end of the compartment, the retainer including an inner piece and an outer piece mounted on the inner piece so as to be rotatable about the inner piece and constrained from movement relative to the inner piece in the longitudinal direction; and
at least one acceptance in the retainer; and
an implantable medical device assembled in the compartment, the medical device having at least one retention member at an end thereof, the retention member being positioned in the acceptance,
wherein the outer piece has a retention edge facing the compartment and the acceptance has a first region sized to receive the retention member, the acceptance including at least one protuberance defining a narrowed neck between the first region and the retention edge.

9. The system of claim 8, wherein one of the outer piece and the inner piece includes a circumferentially extending groove and another of the outer piece and the inner piece includes an annular ring assembled in the groove and permitting the outer piece to rotate about the inner piece.

10. The system of claim 9, wherein the retainer further includes a support piece mounted on the inner piece and fixedly connected to the outer piece, whereby the outer piece and the support piece are rotatable together about the inner piece.

11. The system of claim 8, wherein the medical device includes a self-expanding stent having a plurality of struts and the outer piece has a retention edge facing the compartment and at least one recess extending in the longitudinal direction from an open end at the retention edge to a closed end, one of the plurality of struts at an end of the stent being assembled in the recess.

12. The system of claim 11, wherein the acceptance has a length in the longitudinal direction such that the one of the plurality of struts contacts the closed end of the recess while the retention member is spaced from a closed end of the acceptance.

13. The system of claim 8, further comprising:
a pin extending radially outward from the at least one acceptance and engaged in an aperture in the retention member; and
an actuator coupled to the pin and adapted to move the pin in the longitudinal direction, thereby adjusting the longitudinal position of the retention member relative to the acceptance.

14. The system of claim 8, wherein the medical device is a self-expanding collapsible prosthetic valve.

15. A delivery device for an implantable medical device including a self-expanding stent having a plurality of struts and at least one retention member at an end of the stent, the delivery device comprising:
a shaft extending in a longitudinal direction;
an elongated sheath surrounding a longitudinal portion of the shaft, the sheath being slidable relative to the shaft in the longitudinal direction;
a compartment defined inside of the sheath and adapted to receive the medical device in an assembled condition;
a retainer positioned at one end of the compartment, the retainer having a retention edge facing the compartment;
at least one acceptance in the retainer adapted to receive the retention member of the medical device in the assembled condition, the acceptance extending in the longitudinal direction from an open end at the retention edge to a closed end facing in a first direction towards the compartment, the acceptance having a length in the longitudinal direction such that in the assembled condition the length of the acceptance is greater than a length of the retention member in the longitudinal direction; and
at least one recess in the retainer, the recess adapted to receive one of the plurality of struts at the end of the stent of the medical device in the assembled condition, the recess extending in the longitudinal direction from an open end at the retention edge to a closed end facing in the first direction towards the compartment,
wherein in the assembled condition the one of the plurality of struts contacts the closed end of the recess while the retention member is spaced from the closed end of the acceptance, the closed end of the recess located a first distance from the retention edge in the longitudinal direction, the closed end of the acceptance located a second distance from the retention edge in the longitudinal direction, the second distance being greater than the first distance.

16. The delivery device of claim 15, wherein the acceptance has a first region sized to receive the retention member, the acceptance including at least one protuberance defining a narrowed neck between the first region and the retention edge.

17. The delivery device of claim 15, further comprising the implantable medical device disposed in the compartment in the assembled condition.

18. The delivery device of claim 17, wherein the medical device is a self-expanding collapsible prosthetic valve.

19. The delivery device of claim 17, further comprising:
a pin extending radially outward from the at least one acceptance, the pin being adapted to engage an aperture in the retention member; and
an actuator coupled to the pin and adapted to move the pin in the longitudinal direction, thereby adjusting the longitudinal position of the retention member relative to the acceptance.

* * * * *